United States Patent
Squires

(10) Patent No.: US 6,946,490 B2
(45) Date of Patent: Sep. 20, 2005

(54) ANTIMICROBIAL TREATMENT FOR HERPES SIMPLEX VIRUS AND OTHER INFECTIOUS DISEASES

(76) Inventor: Meryl Squires, 2 Goose Lake Dr., Barrington Hills, IL (US) 60010

( * ) Notice: Subject to any disclaimer, the term of this patent is extended or adjusted under 35 U.S.C. 154(b) by 137 days.

(21) Appl. No.: 10/093,093

(22) Filed: Mar. 7, 2002

(65) Prior Publication Data

US 2003/0099726 A1 May 29, 2003

Related U.S. Application Data

(63) Continuation of application No. 08/646,988, filed on May 8, 1996, now Pat. No. 6,355,684, which is a continuation-in-part of application No. 08/600,217, filed on Feb. 12, 1996, now Pat. No. 6,348,503.

(51) Int. Cl.$^7$ ................................................. A61K 31/14
(52) U.S. Cl. ..................... 514/643; 514/642; 514/53; 514/54; 514/28; 514/33; 514/456
(58) Field of Search ................... 514/28, 33, 53, 514/54, 642, 643, 456

(56) References Cited

U.S. PATENT DOCUMENTS 4,797,420 A * 1/1989 Bryant ........................ 514/643
6,348,503 B1 * 2/2002 Squires ....................... 514/642
6,355,684 B1 * 3/2002 Squires ....................... 514/643

FOREIGN PATENT DOCUMENTS

EP          308564 A1 *  3/1999

OTHER PUBLICATIONS

Typler, V.E., "The Honest Herbal, A Sensible Guide to the Use of Herbs and Related Remedies", 3rd Edition, pp. 115–117, 199.*
Tyler, V.E., "The Honest Herbal, The Therapeutic Use of Phytomedicinals", 3rd Edition, pp. 181–186, 1994.*
Abstract to EP 308564 A1, Bourbon et al.*

* cited by examiner

*Primary Examiner*—Dwayne C. Jones
(74) *Attorney, Agent, or Firm*—Welsh & Katz, Ltd.; Thomas W. Tolpin

(57) ABSTRACT

An improved medical treatment and medicine is provided to quickly and safely resolve herpes and other microbial infections. The inexpensive user-friendly medicine can be applied and maintained on the infected region until the physical symptoms of the disease disappears and the patient is comfortable and has a normal appearance. The attractive medicine comprises an antimicrobial concentrate comprising microbe inhibitors, phytochemicals or isolates. Desirably, the effective medicine comprises a surfactant and an aqueous carrier or solvent. In the preferred form, the medicine comprises *Echinacea* phytochemicals and benzalkonium chloride in a sterile water solution.

10 Claims, No Drawings

ANTIMICROBIAL TREATMENT FOR HERPES SIMPLEX VIRUS AND OTHER INFECTIOUS DISEASES

This application is a continuation of U.S. Ser. No. 08/646,988 filed on 8 May 1996, now U.S. Pat. No. 6,355,684, which in turn is a continuation-in-part of U.S. Ser. No. 08/600,217 filed on Feb. 12, 1996, now U.S. Pat. No. 6,348,503.

BACKGROUND OF THE INVENTION

The present invention relates to herpes virus, and more particularly, to medical treatments for herpes virus and other microbial infections.

Herpes simplex virus (HSV) commonly referred to as "herpes virus" or "herpes," is an infectious disease which has reached crisis proportions nationally with estimated numbers of infected people at 70%–80% of our population as reported by the American Social Health Association (ASHA) and growing annually by 500,000 people or more. There are two common types of herpes: herpes simplex virus 1 (HSV 1) and herpes simplex virus 2 (HSV 2).

Herpes enters the human body through minuscule breaks in the epidermal tissue usually by contact with an infected host and is marked by eruption of one or more vesicles, usually in groups, following an incubation period of approximately four to ten days. Typically the course of the infectious outbreak initiates with the prodromal stage; advancing to vesicular eruption; followed by: ulceration; coalescing; resolution; and the latency period. The outbreak can last for several weeks and on average lasts two-three weeks. In some immune compromised individuals the outbreak can last for months. The vesicles can appear anywhere on the skin or mucosa, typically appearing on the lips as cold sores, glands, oral mucosa, conjunctiva and cornea, genitalia, anal mucosa and peri-anal tissue.

Herpes symptoms include: inguinal swelling, pain, fever, malaise, headaches, muscle aches, and swollen glands. Some individuals with trigeminal nerve affected oral herpes, have excruciating facial pain, difficulty swallowing, eating and facial swelling. Individuals with the sacral nerve effected have severe upper leg pain, swelling, and great difficulty walking.

Herpes simplex virus (HSV) infection is recrudescent, residing in the nerve ganglia, then recurring due to some, as yet unknown, stimulus. Recurrent herpetic infections can be precipitated by almost anything, including: overexposure to sunlight; nutritional deficiencies; stress, menstruation; immunosuppression; certain foods; drugs; febrile illness; etc. Recently herpes virus was isolated from cardiac tissue.

HSV 1 and HSV 2 infections pose very serious health threats often causing: blindness; increased cancer risk of the cervix; aseptic meningitis and encephalitis; neonatal deaths; viremia; etc. The devastating effects of this disease, go well beyond the medical scope of human suffering; HSV is responsible for serious psychological and emotional distress as well as substantial economic loss to the nation and the world.

Various treatments for herpes have been proposed and have included topical application of such agents as povodoneiodine, idoxuridine, trifluorothymidine, or acyclovir. Such treatments have met with varying degrees of success. Most prior treatments have proven disappointing. Acyclovir, taken orally for systemic treatment of HSV, is somewhat effective. However, acyclovir is only successful in interrupting the replication of the virus and is used to treat infectious outbreak systemically. Nothing to date has proven really effective topically. Strains resistant to acyclovir have been reported. Individuals with Auto Immune Deficiency Syndrome (AIDS) are seriously immune-compromised and suffer especially debilitating outbreaks of HSV. Additionally, AIDS individuals may carry acyclovir resistant strains of HSV, which can make acyclovir ineffective for these individuals.

It is, therefore, of utmost importance to develop a safe and successful medical treatment to overcome the very serious problems of herpes virus.

SUMMARY OF THE INVENTION

An improved medical treatment and medicine are provided which, when applied in the topical manner, rapidly relieves pain and heals lesions of herpes virus. Advantageously, the improved medical treatment and medicine are safe, inexpensive and effective. The improved medicine, also referred to as Viracea, comprises a novel medical composition, formulation, antimicrobial compound and solution. The new antimicrobial medical treatment and microbicidal medicine are successful in treating primarily herpes simplex virus (HSV 1 & HSV 2) topically and can be useful in treating other herpes related microbial infections including, but not limited to: varicella zoster virus (herpes zoster) and cytomegalovirus. In some circumstances, it may be useful to use the novel medicine systemically.

Advantageously, the improved medical treatment and medicine of the present invention yielded unexpected, surprisingly good results. Initial, topical, in vivo testing, demonstrated relief from pain in minutes and speedy total resolution of vesicular eruption in all individuals tested. When the inventive medical treatment and medicine are applied at the prodromal stage, the infection is interrupted and no further outbreak occurs. In vitro testing of the novel medical treatment and medicine demonstrated extremely surprising inhibitory effects on herpes virus. Desirably, the novel medicine is made from readily available, over the counter (OTC) chemicals or products and provides a safe comfortable, economical and user-friendly treatment.

While the novel medicine and antimicrobial compound is particularly useful in dramatically inhibiting herpes virus simplex, it may be useful in treating other microbial diseases (microbe-causing diseases)such as: human immunodeficiency virus infection (HIV), Epstein barr, papilloma virus, cellulitis, staphylococci, streptococci, mycobacteria, influenza, parainfluenza, adenoviruses, encephalitis, meningitis, arbovirus, arenavirus, anaerobic bacilli, picornavirus, coronavirus and synsytialvirus, as well as varicella zoster virus and cytomegalovirus.

This easy to use microbicide solution provides a moderately water resistant coating upon application to either the prodromal tissue or the erythematous vesicular herpes lesion. Upon contact, there is a slight tingling effect. Within minutes of application, the pain of the infection resolves. Gradually, inguinal swelling subsides, fever, malaise, body aches, and nerve involvement subsides. Typically, within twenty-one hours all external symptoms and physical manifestations of infection are resolved and the vesicle is dried and resolved. A particularly surprising, beneficial effect provided by this inventive medicine, is that when it is applied at the first sign of outbreak, the prodromal stage, all symptoms and signs of further infectious outbreak stops! No eruptions appear or any further escalation of symptoms of the infection. The outbreak literally stops!

Desirably, the novel medicine (medical composition) includes microbe inhibitors which inhibit, suppress and stop microbial infections from microbe-causing diseases. The microbe inhibitors comprise antimicrobial isolates, botanical extracts or phytochemicals, of at least a portion of one or more of the special plants listed below. The microbe inhibitors can comprise viral inhibitors to inhibit viral diseases, such as: herpes simplex virus 1 (HSV 1), herpes virus 2 (HSV 2), varicella zoster virus (herpes zoster), cytomegalovirus, HIV, epstein barr, papilloma virus, viral influenza, viral parainfluenza, adenovirus, viral encephalitis, viral menigitus, arbovirus, arenavirus, picornavirus, coronavirus, and synsytialvirus. The microbe inhibitors can also comprise bacterial inhibitors to inhibit bacterial diseases, such as: cellulitis, staphylococci, streptococci, mycobacteria, bacterial encephalitis, bacterial meningitis, and anaerobic bacilli. In some circumstances, the microbe inhibitors can include fungi inhibitors.

Better results are obtained if *Echinacea* or other plants are not used in the medicine in their raw, untreated and uncut state. For even better results, the medicine can exclude: Arabinose, betaine, cellulose, copper, fructose, fatty acids, galactose, glucose, iron, potassium, protein, resin, sucrose, sulfur, vitamin a, vitamin c, vitamin e and xylose.

The improved medical treatment provides a novel method and process for use in treating the above infectious diseases by applying the microbial inhibitors on the microbial infected area and maintaining the microbe inhibitors on the infected area (region or surface) until the external symptoms and physical manifestations of the infection disappear, reside or resolve about the infected area. The medicine can be applied by spraying, dabbing, dusting, swabbing, sponging, brushing, pouring, dispensing, covering, or heavily coating the medicine on the microbial infected areas, such as: oral mucosa, nasal mucosa, vaginal tissue, labial tissue, anal tissue, peri-anal tissue, lips, cutaneous tissue, sub-cutaneous tissue, ocular tissue, conjunctiva, and eyelids.

While the medical treatment and medicine is particularly useful for inhibiting herpes and other infectious diseases in persons (human beings) (homo sapiens), they can also be useful for veterinary purposes for treating viral and bacterial infections and infectious diseases in animals, such as: dogs, cats, birds, horses, cows, sheep, swine (pigs and hogs), and other farm animals, as well as rodents and other animals seen in zoos.

Preferably, the improved medicine, medical composition or microbial compound is a phytochemical concentrate which is combined and simultaneously or concurrently applied with a surfactant and a carrier, solvent or diluent to provide a microbicide medicinal solution.

To this end, the interesting microbicide solution comprises an antimicrobial detergent surfactant, with botanical extracts. The surfactants preferably are cationic surfactants which can comprise singly or any number of quaternary ammonium chlorides having 6–18 carbons such as alkylbenzyldimethylammonium chloride, mixtures of alkylbenzyldimethylammonium chloride, alkyldimethyl/ethylbenzylammonium chloride, n-alkyldimethylbenzylammonium chloride, diisobutylphenoxyethoxyethyldimethylbenzylammonium chloride, N-$(C_{12}C_{14}C_{16})$ dimethylbenzylammonium chloride, benzalkonium chloride, octyldecyldimethyloammonium chloride, didecyldimethylammonium chloride, dioctyldimethylammonium chloride, dialkyldimethylammonium chloride, dialkylmethylbenzylammonium chloride, octyldecyldimethylammonium chloride, dimethylbenzylammonium chloride, laurryldimethylbenzylammonium chloride, o-benzyl-p-chlorophenol, dideryldimethylammonium chloride, doctyldimethylammonium chloride, alkyl $(C_{14}C_{12}C_{16})$ dimethylbenzylammonium chloride, and preferably comprises alkylbenzyldimethylammonium chloride most preferably benzalkonium chloride. The range of activity of the cationic surfactant can be 5% to 90% but for best results 8% to 20%. Quaternary ammonium salts are readily available commercially. In some circumstances it may be useful to use other surfactants, such as, but not limited to: DMSO, glycolic acid surfactants, enzyme surfactants, ampholytic surfactants, switterionic surfactants, and non-ionic surfactants. The surfactants can comprise detergents, wetting agents, emulsifiers, defoamers, and/or surface tension reducing additives.

Carriers are useful for mixing the constituents, keeping the constituents in solution, and providing an easy method of application to the affected area whether by spray, dropper, or applicator. While an aqueous solution, preferably a sterile aqueous carrier and solvent is preferred for best results, in some circumstances it may be desirable to use other liquid or solid carriers, such as: glycerin, mineral oil, silica, cottonseed oil, coconut oil, vegetable oil, seed oil, fish oil, or animal oil, alcohol, talc, corn meal, beeswax, carnauba wax, beta carotene, garlic oil, camphor oil, soluble vitamins, soluble minerals, rape seed oil, nut oils, olive oil, liposomes, ascorbic acid, evening primrose oil, pycnogenol, grape seed oil, lanolin, Ethocyn, collagen, aloe vera, bee pollen, royal jelly, chondroitin sulfate A, sea vegetables, EDTA, fatty acids, herbs, lecithin, bioflavinoids, grain oils or powders, algae, teas, vinegars, acidophilus, cell salts, ascorbic acids, hydra 5, glandulars, amino acids, psyllium, plant derivatives, or other sterile carriers.

The botanical extracts antimicrobial isolates or phytochemicals contained in this new medicine and medical treatment can be comprised of: Arabinose, betaine, copper, echinacen, echinacin B, echinacoside, echinolone, enzymes, fructose, fatty acids, galactose, glucose, glucuronic acid, inulin, inuloid, iron, pentadecadiene, polyacelylene compounds, polysaccharides such as but not limited to arabinogalactan, potassium, protein, resin, rhamnose, sucrose, sulfur, tannins, vitamins a, c, and e, xylose. For better results, the phytochemical concentrates include the above phytochemicals, excluding Arabinose, bataine cellulose, copper, fructose, fatty acids, galactose, glicose, iron, potassium, protein, resin, sucrose, sulfer, xylose and vitamins a, c and e.

The botanical extracts, antimicrobial isolates and phytochemicals are separated, extracted and isolated from portions of plants, such as: pimpinella anisum, myroxylon, arctostaphylos, carum, capsicum, eugenia mytacea, coriandrum, inula, allium, gentiana, juniperus, calendula, origanum, mentha labiate, commiphora, plantago, rosmarinus, ruta, baptisa, artemisa, sage, mentha, parthenium integrifolium, eucalyptus, asteriacea, and preferably from the genus Echinacea of the family Astericaea, namely, *Echinacea purpurea, Echinacea angustofolium, Echinacea pallidae, Echinacea vegetalis, Echinacea atribactilus* and their cultivars. For best results, the phytochemicals and antimicrobial isolates are extracts from *Echinacea purpurea* and *Echinacea angustifolium*.

The inventive technology, treatment and medicine yield very attractive, unexpected, surprisingly good and consistent results. Tests show the microbicide solution (medicine) and medical treatment to be extremely useful to: heal and control herpes outbreaks, viral shedding, extend the latency periods of the disease, and dramatically inhibit the virus, while being generally safe to the patient and the environment.

A more detailed explanation of the invention is provided in the following description and appended claims.

DETAILED DESCRIPTION OF THE PREFERRED EMBODIMENTS

A herpes virus microbicide and treatment are provided to ease pain, heal lesions, resolve infectious outbreaks rapidly and inhibit herpes simplex virus 1 and 2 (HSV 1 & HSV 2). Desirably, the herpes microbicide and treatment completely inhibits herpes virus, as well as other infectious microbial diseases, and are safe and non-toxic to humans, animals, and the environment.

The herpes microbicide and medicine can comprise a surfactant and an herbaceous botanical providing a botanical extract, phytochemical, antimicrobial isolate, viral isolate, microbe inhibitor, and viral inhibitor. The preferred microbicide composition can comprise: a surfactant; an aqueous diluent; and the herbaceous botanical of the genus Echinacea (E), of the family Asteracea, species: purpurea, angustifolia, pallidae, vegetalis, atribactilus and the cultivars. Preferably, the herbanaceous botanicals are extracts and isolates comprising Echinecea phytochemicals as found in and extracted from Echinacea purpurea, E. pallidae, and E. angustofolia. For best results, the medical treatment and microbicide (medicine) comprises: a cationic surfactant; the phytochemicals from E. purpurea, and E. angustofolia; and a sterile aqueous diluent.

The surfactant provides a certain debridement of epithelial cells with a broad spectrum of antimicrobial action. Surfactants of this nature can comprise quaternary ammonium salts containing 6–18 carbon atoms. Preferably the quaternary ammonium salt surfactant, is a mixture of alkyl dimethylbenzylammonium chlorides, which can be: benzalkonium halide, benzalkonium bromide, benzalthonium chloride and most preferably benzalkonium chloride. The herpes treatment comprises a 100% active aqueous solution but can also be used in concentrate. The solution can comprise by weight various concentrations of surfactants such as 0.005% to 0.8%, preferably 0.02% to 0.30% and most preferably 0.02% to 0.26%.

The phytochemicals in the botanical Echinacea have demonstrated impressive activity against bacteria, viruses, and some fungi. The exact mechanism is unknown. When tested topically in vivo on HSV 1 & 2, it is somewhat effective in treating herpes simplex infectious outbreaks. When tested in vitro, it showed some inhibitory activity against HSV 1 & 2.

The phytochemical concentrate composition comprises the following isolated constituents, botanical extracts, microbial inhibitors, and antimicrobial isolates: polysaccharides, echinacen, echinaceine, echinacoside (caffeic acid ester) echinolone, echinadiol, enzymes, glucuronic acid, inuloid, pentadecadiene, polyacelylene compounds, arabinogalactan, rhamnose, PS I (a 4-0-methylglucoronoarabinoxylan, $M_r$ 35 kD) and PS II (an acid rhamnoarabinogalactan, $M_r$ 450 kD), cynarin (1,5-di-0-caffeoylquinic acid), acid (2,3-0-di-caffeoyltartaric acid) and derivatives, alkylamides, keto-alkynes and -alkenes; quinones; oils including: borneol, bornyl acetate; pentadeca-8(z)-en-2one, germacrene D, caryophyllene, caryophyllene epoxide, anthocyanins pyrrolizidine alkaloids, lipophilic amides, isobutylamides, polyacetylenes.

For best results, the antimicrobial isolates of the phytochemical concentrate comprise by weight (based upon the total weight of the inventive medical composition): 0.3–9% echinacoside; 0.1–7% PS I (a 4-0-methylglucoronoarabinoxylan, $M_r$ 35 kD) and PS II (an acid rhamnoarabinogalactan, $_r$M 450 kD); 0.1–10% cynarin (1,5-di-0-caffeoylquinic acid) and acid (2,3-0-di-caffeoyltartaric acid) and derivatives; 0.2–4% echinolone; 0.2–8% echinacin B; 0.1–6% echinaceine; 0.2–7% anthocyanins comprising cyanidin 3-0-β-D-glucopyranoside and 3-0-(6-0-malonyl-β-D-glucopyranoside); 0.01–0.06% pyrrolizidine alkaloids comprising tussilagine and isotussilagine; 0.003–0.009% isomeric dodeca isobutylamides and 2E, 4E,8Z, 10E/Z-tetraenoic acid; and 0.01–2% caryopylenes.

The phytochemical concentrate can comprise by weight: 2%–90% of the medical composition and solution and preferably comprises not less than 15% of the composition and solution; and for best results, comprises 40%–60% of the medical composition and solution.

The diluent dissolves the benzalkonium chloride (surfactant) and phytochemical concentrates and can act as a carrier in sprays, tubes, and dropper bottles. The preferable diluent is an aqueous diluent and most preferably is a sterile aqueous diluent. The ratio of water in the aqueous solution to benzalkonium chloride can range from 30,000:1 to 250:1 and preferably in topical application from 5000:1 to 750:1. The ratio of water to the combined concentrates of benzalkonium chloride and phytochemicals can comprise a range of 2:1 to 100:1 with a preferable range of 4:1 to 40:1, and for best results can comprise a ratio of 6:1 to 20:1.

For best results, the improved microbicidal treatment and medicine (microbicide) for herpes, comprises by weight: 0.02% to 0.3% benzalkonium chloride and to avoid toxicity preferably less than 0.26%; 40% to 60% Echinacea phytochemicals; and 20% to 60%, most preferably 29.74% to 59.8% sterile water.

While water is the preferred diluent and carrier, it may be desirable in some circumstances to use other carriers in order to propel the concentrate through a sprayer, or for greater solubility and efficacy. It may also be desirable in some circumstances to include a viscosity control agent. Furthermore, while it is estimated that the shelf life of the improved herpes medicine is two years, it may be necessary to add an appropriate preservative.

For preferred use, during any outbreak or physical manifestations of herpes and preferably at the first sign of the prodrome stage of tingling, itching, or irritation of herpes, the medical solution (medicine) should be applied topically on the infected area. The affected (infected) area should be as dry as possible depending on location of outbreak. The method of topical application of medicine can be by: spraying, dabbing, dropper, or any such method as to coat the entire affected area. The coating of the solution (medicine) should be maintained until all external symptoms completely resolve, reapplying as needed anytime the coating diminishes, for instance, after showering. Anionic soaps and anionic detergents, and especially protein content soaps can be contraindicated. Preferably, the infected area should be washed, cleaned and dried prior to application of the medicine.

Clinical Pharmacology

A preferred surfactant is benzalkonium chloride. Benzalkonium chloride in aqueous solution is commercially available under the brand name and trade mark Zephiran® distributed by Sanofi Winthrop Pharmaceuticals (formerly Winthrop Labs). Benzalkonium chloride is a rapidly acting anti-infective surfactant with a moderately long duration of action. The surfactant is active against bacteria and some viruses, fungi and protozoa. Bacterial spores are considered to be resistant. Solutions of benzalkonium chloride are bacteriostatic or bacteriocidal according to concentration. The exact mechanism of bacterial action of benzalkonium chloride is unknown but is thought to be due to enzyme inactivation. Activity of benzalkonium chloride generally increases with increasing temperature and pH. Gram-positive bacteria are more susceptible to benzalkonium chloride than gram-negative bacteria.

Unfortunately, benzalkonium chloride is inactivated by soaps, anionic detergents, serum, and certain proteins. Benzalkonium chloride has fallen out of favor in many laboratories for the above reasons. When benzalkonium chloride was used alone and tested topically in vivo, it was ineffective for herpes simplex infectious outbreaks. When tested in vitro on HSV1 & 2 benzalkonium chloride demonstrated undesirable high levels of toxicity to the cells even at high dilutions, which is medically unacceptable. The chemical formula of one type of benzalkonium chloride is shown below. Other types of benzalkonium chloride can be used.

Benzalkonium Chloride

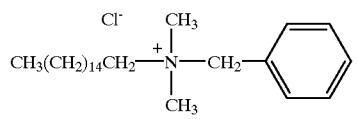

While raw, untreated, unprocessed, non-isolated Echinacea is generally undesirable to treat herpes, it has been found that some, but not all, of the isolated constituents and botanical extracts of *Echinacea* (as previously described above) provide phytochemicals, antimicrobial isolates, botanical extracts and microbe inhibiters which are effective in treating herpes virus and other infectious diseases. As previously stated, the phytochemical concentrate composition comprises the following isolated constituents, botanical extracts, microbial inhibitors, and antimicrobial isolates: polysaccharides, echinacen, echinaceine, echinacoside (caffeic acid ester), echinolone, echinadiol, enzymes, glucuronic acid, inuloid, pentadecadiene, polyacelylene compounds, arabinogalactan, rhamnose, PS I (a 4-0-methylglucoronoarabinoxylan, $M_r$ 35 kD) and PS II (an acid rhamnoarabinogalactan, $M_r$ 450 kD), cynarin (1,5-di-0-caffeoylquinic acid), acid (2,3-0-di-caffeoyltartaric acid) and derivatives, alkylamides, keto-alkynes and -alkenes; quinones; oils including: borneol, bornyl acetate; pentadeca-8 (z)-en-2one, germacrene D, caryophyllene, caryophyllene epoxide, anthocyanins pyrrolizidine alkaloids, lipophilic amides, isobutylamides, polyacetylenes. The chemical formula of some of the botanical extracts of *Echinacea* are shown below.

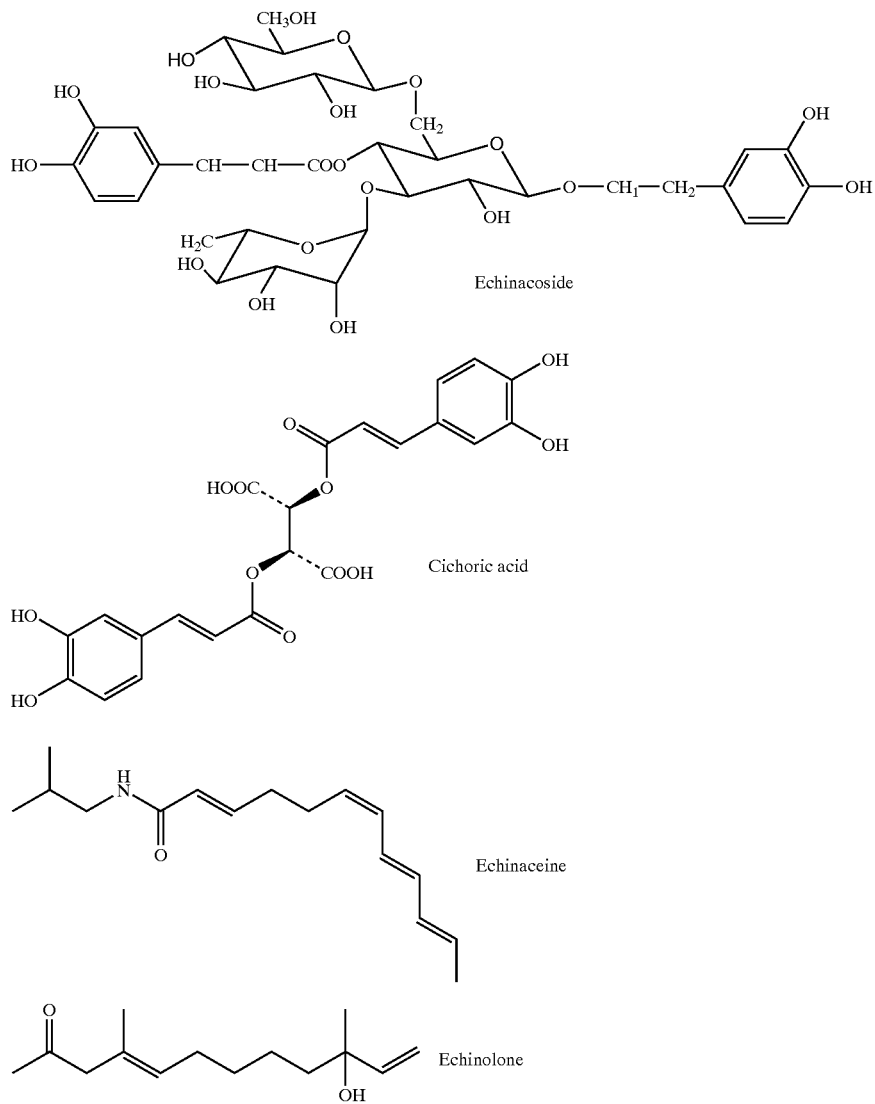

When the *Echinacea* phytochemicals (antimicrobial isolates, botanical extracts and microbe inhibitors) were mixed, combined and applied with a surfactant, preferably benzalkonium chloride, and a sterile aqueous carrier, the results were unexpected and surprisingly good in resolving (treating) herpes virus and other infectious diseases and the effectiveness of the medicine (microbicide) dramatically increased. When the synergistic medicine was tested topically in vivo, the herpes simplex infections were immediately arrested. When the synergistic medicine was tested in vitro, the benzalkonium chloride surfactant was substantially less toxic and within a safe level and there was a higher level of inhibitory activity against HSV 1 & 2. The synergism interaction and mixing of the *Echinacea* phytochemicals and surfactant were demonstrated and observed by viewing the rapid solubility of the components when mixed and the slight adhesive quality created by the properties in solution. Furthermore, the chemical properties of the *Echinacea* phytochemicals, surfactant and aqueous carrier enhanced stabilization and increased reactivity which is useful in treating infectious diseases.

The medicine can be used in varying dilutions on: oral and nasal mucosa; vaginal tissue; labial tissue; anal and peri-anal tissue; penile tissue; cutaneous tissue; open subcutaneous tissue; and in higher dilutions on ocular infections. By varying the concentrations, the medicine may possibly be administered parenterally. The medicine may be contraindicated in vaginal or anal packs; in the ear canal; occlusive dressings; casts or ingestion and such use may produce irritation or chemical burns. It may not be advisable to use the medicine to treat anaerobic fungal infections, since some fungi may be resistant.

EXAMPLES 1–7

In Vivo Testing

In an initial, topical application, in-vivo study that was undertaken to evaluate the effects of the medical treatment and medicine of the present invention upon seven human test subjects who had been tested positive for HSV 1 or 2. The subjects were treated topically with the medicine comprising benzalkonium chloride surfactant in an aqueous solution (at a ratio of 1:750) in combination with the herbaceous botanical *Echinacea purpurea* in powdered form containing the previously listed phytochemicals. Application of the composition was made by a two-step procedure by first wetting the affected area or vesicle with the benzalkonium chloride surfactant in an aqueous solution by spraying, dabbing, or using a dropper; then applying a coating of the powdered phytochemicals over the wetted area by either swab or manually sprinkling the powder onto the infected area. An important aspect in this treatment was maintaining complete coverage of the affected area for the duration of the outbreak. Therefore, the area of outbreak was kept covered with the medical composition by reapplying as needed.

Of the seven subjects, six were female, and one was male. At the beginning of this study, the age of the male was 38, the female subjects were ages 8, 27, 30, 32, 38, and 39. There were twelve infectious outbreaks over approximately six weeks. Nine of the outbreaks were HSV 2, genital herpes, and three were HSV1, cold sores. The 8 year old and the 27 year old females exhibited the HSV 1 (cold sores). The 30 year old, 38 year old and the 39 year old females exhibited the HSV 2 (genital herpes). The 38 year old also had a HSV 1 cold sore. The male exhibited HSV 2 (genital herpes). All subjects tested had a well established history of the disease and could identify the standard course of their disease. To obtain objective data, none of the test subjects knew anything about the test treatment or any action of the medicine. On repeat tests, the subjects were told that there may be placebos mixed in the samples of formula.

In seven cases, the antimicrobial compound (medicine) was applied directly on tissue at the prodrome stage. In five cases, the antimicrobial compound was applied directly on erupted vesicles. The antimicrobial compound was reapplied as necessary to maintain coverage.

Observations: With each application of the medicine, each individual (test subject) reported a tingling sensation for a few seconds. They also reported that there was a substantial degree of adherence of the medicine (antimicrobial) compound to the vesicle(s) or affected area. The adherence of the composition to the epithelial tissue remained to a degree even after showering or water rinsing the area.

Results: The results of the testing of the 7 subjects with the medical treatment and medicine were unexpectedly surprisingly good and very consistent. In each case, the subject happily reported that once the composition (medicine) was applied to the affected area, the pain completely stopped within 10 to 20 minutes when nothing in the past had ever eased pain before. In the seven cases, where the compound (medicine) was applied at the prodrome stage, the subjects reported that the pain stopped, all symptoms that would have previously escalated to full outbreak ceased and the outbreak never occurred. All external symptoms and physical manifestations of herpes disappeared within a few hours after the medicine was applied. In the five cases, where the compound (medicine) was applied to erupted vesicles, the subjects reported that the pain stopped in minutes and the burning, itching and irritation resolved in two to four hours and the vesicles dried up and were gone in twenty-one hours. In all cases, the other more extreme, debilitating symptoms of: fever, malaise, inguinal swelling, weeping sores and painful urination resolved once the medicine was applied.

In follow-up, where subjects had been given a supply of the composition (medicine) to test on future outbreaks, it was reported that if the initial signs of an outbreak exhibited, signaling the prodrome stage of an outbreak, the compound (medicine) was immediately applied by the subjects as per instructions and the outbreak was fully arrested and further symptoms never occurred. Significantly, it was also reported by subjects who were accustomed to experiencing several outbreaks annually, that they had remarkably longer latency periods. In a three year follow-up, one individual who had reported severe outbreaks monthly for four years prior to use of this medicine, she now reports that she has not had an outbreak in over a year since using this medicine.

Additional Observations: One human male subject reported that after the initial application during the prodrome phase of an outbreak, he showered and forgot to reapply the composition (medicine) for a period of approximately 30 hours. Consequently, several vesicles erupted and began to coalesce. The subject proceeded to reapply the composition (medicine) and thereafter kept the area well coated with the composition. Subsequently, the outbreak resolved in 21 hours in the same manner as described with the other human subjects.

Another observation indicated that the composition (medicine) may be weakened or less effective in the presence of certain proteins or soaps. One human female subject, may have been overly zealous in cleansing the affected area prior to application of the composition (medicine). This occurred during a third outbreak after having success with the composition (medicine) on two prior outbreaks. In this instance, when the composition (medicine) was applied, there was no familiar tingling sensation and no relief from symptoms. Approximately 24 hours elapsed before she sought any advice and the outbreak had escalated to the full vesicular eruption stage with all the foregoing symptoms of the disease. She was instructed to thoroughly rinse any soap residue from the area, dry the area and reapply the composition (medicine). After following the instructions, she reported that the outbreak fully resolved, as it had in the two prior outbreaks, after applying the medical composition.

EXAMPLES 8–13

Dermatological and Veterinary Testing

Animal testing to determine any possible dermatological allergic reaction induced by the medical composition (medicine) was undertaken. Six animal subjects were used. The animals included 3 female rabbits (ages unknown); 2 dogs (1 female 2 year old, and 1 male 9 year old); one, 3 year old neutered male cat. In these animal tests, the above composition (medicine) was applied, in the previously stated method, to the inside of the outer ear of each animal. In all instances, the area being treated was kept coated with the compound for twenty-four hours, matching the time human subjects had used. The testing performed on the six animal subjects indicated that there were no signs of dermatological irritation or allergic reaction.

EXAMPLE 14

The above medical compound containing viral inhibitors was also tested on a papilloma virus caused wart on the muzzle of a two year old gelded thoroughbred horse. Papilloma virus warts are difficult to treat. The wart measured 25 mm in diameter. The antimicrobial compound (medicine) was applied twice daily. The wart was then measured at each application.

Results: Quite unexpectedly, the wart decreased dramatically in size by approximately 3 mm per day while the medicine was applied to the wart and on the fifth day fell off completely. It was observed that, at first the surface layers of the wart began to degrade, exposing large erythematous papules. Then interestingly, the warts did not just diminish in size by flaking or peeling, they diminished at the point of attachment on the subject's epidermis and fell off still somewhat intact with no sequela scarring.

In an ongoing, long term in vivo study of this invention, which began with the first seven subjects in April of 1989 and has now spanned 7 years, approximately 100 infectious outbreaks have been treated with the medicine in different concentrations, as described previously. In all cases the surprisingly good results were the same: 1. Pain disappears in minutes; 2. No outbreak occurs when the composition is applied at the prodrome stage; 3. The outbreak resolves in twenty-one hours when applied at the vesicular stage; 4. Longer latency periods or no further outbreaks.

In Vitro Testing

Laboratory testing was undertaken at the University Of Chicago, Clinical Microbiology Laboratories to determine inhibitory activity in vitro of the medical treatment and composition (medicine). The laboratory testing was conducted by the Associate Director, PhD, and Associate Professor of Pathology. The in vitro testing of the medical composition, referred to as the "Drug" below, yielded surprisingly good results. It was determined that the medical treatment and composition had unexpectedly, surprising excellent inhibitory activity on HSV 1 and HSV 2. It was stated by the pathologist, that he had tested "hundreds" of other compounds and had never seen anything as good as what this compound did.

The following are the tests of the medicine that were conducted and results that were obtained at The University of Chicago. For ease of interpreting some of the scientific data and test results, the following definitions apply:

"MEM" pertains to Minimal Essential Medium. This is the culture medium used in laboratories for growing the cells upon which tests will be run.

"Fibroblast" is a mesenchyme human cell (a cell found in connective tissue, blood, bone, lymphatics, and cartilage).

"$IC_{50}$" pertains to the Inhibitory Concentrate. For this testing a 50% endpoint was selected, as is typical. The number following indicates the greatest dilution below 50%. Therefore it is the definition of the endpoint.

If an area under a dilution is left blank, it indicates that there may have been toxicity at that dilution, the test may not have been worth reading, or no interpretable data is available.

If an area under dilution is marked with a hyphen (-), it indicates that there are no plaques and there is total successful inhibitory activity.

EXAMPLES 15–18

In these in vitro tests, the following drugs (composition) was used:

Drug # 1.=Benzalkonium chloride surfactant in an aqueous solution at a ratio of 1:750. The surfactant in the aqueous solution was filtered before use and diluted in an equal volume of 2× MEM to give a 1:1500 dilution in 1×MEM.

Drug # 2=Echinacea powder (photochemicals) in an aqueous solution. This preparation was extracted by warm infusion in sterile water. The extracted phytochemicals was centrifuged and filtered before use. The filtered phytochemicals were diluted in an equal volume of 2×MEM to give the undiluted preparation in 1×MEM.

Drug # 3=*Echinacea* powder (phytochemicals) were extracted and combined with benzalkonium chloride surfactant by a cold infusion process. The combined preparation was centrifuged and filtered before use and diluted in an equal volume of 2×MEM to give the undiluted preparation in 1×MEM.

1. Three 24-compartment plates were inoculated with fibroblasts. Three different extractions (for comparison) in five concentrations of the composition were used to screen for antiviral activity in concentrations of: undiluted, 1:2, 1:4, 1:8, and 1:16 in 1× MEM. There were four control compartments on each plate containing MEM without drug.

2. The growth media was removed from the compartments and 200 ul of HSV-1 was added to each compartment of the upper half of each plate. HSV-1 was diluted 1:5000 (2.0 ul of stock HSV-1 in 10 mL of MEM). The virus titer was $3\times10^6$ per mL. Also, 200 ul of HSV-2 was added to each compartment of the lower half of each plate. HSV-2 was diluted 1:2,000 (5.0 ul of stock HSV-2 in 10 mL of MEM). The virus titer was $6\times10^5$ per mL.

3. The plates were incubated at 37° C. for two hours.

4. The inoculum was removed and one mL of the MEM containing Drugs #1–3 were added to the four compartments. The concentration of the drug compared to the MEM is indicated below.

TABLE 1

| Concentration | Undiluted | 1:2 | 1:4 | 1:8 | 1:16 |
|---|---|---|---|---|---|
| Drug (ul) | 4000 | 2000 | 1000 | 500 | 250 |
| MEM (ul) | — | 2000 | 3000 | 3500 | 3750 |

5. Results: HSV-1, liquid overlay, Drug added immediately after virus absorption.

Plate 1, Drug #1 contaminated with bacteria! No growth, maybe debris.

Plate 2, Drug #2 contaminated with bacteria! No growth, maybe debris.

Plate 3, Drug #3 The results are indicated in Tables 2 and 3 below.

TABLE 2

Drug #3 HSV 1 Test Results

| Concentration | undiluted | 1:2 | 1:4 | 1:8 | 1:16 | |
|---|---|---|---|---|---|---|
| plaques | 54 | toxic | toxic | — | 6* | 12** |
| plaques | 42 | toxic | toxic | — | 4* | 16** |
| Average | 48 | | | | 5 | 14 | $IC_{50} > 1:16$ |

TABLE 3

Drug #3 HSV 2 Test Results

| Concentration | undiluted | 1:2 | 1:4 | 1:8 | 1:16 | |
|---|---|---|---|---|---|---|
| plaques | 46 | toxic | toxic | — | 22* | 32** |
| plaques | 49 | toxic | toxic | — | 21* | 28** |
| Average | 48 | | | | 22 | 30 | $IC_{50} = 1:8$ |

*slight toxicity.
**very small plaques

Comments: Testing with the medicine (Drug #3) provided excellent results. The cells look fine with no contamination. At the lower dilutions, the preparation may be toxic to some of the cells. This preparation was unexpectedly successful in its inhibitory activity.

EXAMPLES 19–22

Three 24-compartment plates were inoculated with fibroblasts and the following drugs.

Test Drug #1A=Benzalkonium chloride surfactant in an aqueous solution. The benzalkonium chloride surfactant was prepared by making a 1:375 dilution in water (32 ul in 12.0 mL of sterile water). This was filtered before use. This was diluted in an equal volume of 2×MEM to give 1:750 dilution in 1×MEM. The dilution was done to maintain the ratio.

Test Drug #2A=*Echinacea purpurea* powder (phytochemicals)

in an aqueous solution. This preparation was a 50 mg/mL solution (300 mg in 6.0 mL of water) of *Echinacea purpurea* powder in sterile water. The mixture was vortexed and refrigerated for four hours. The *Echinacea* powder preparation was centrifuged at 3500 rpm for 15 minutes at 10° C. and filtered before use and then diluted in an equal volume of 2×MEM to give the undiluted preparation in 1×MEM.

Test Drug #3A=*Echinacea purpurea* powder (phytochemicals)

dissolved in benzalkonium chloride surfactant. This preparation was a 50 mg/mL solution (300 mg in 6.0 mL of benzalkonium chloride, 1:375). The mixture was vortexed and refrigerated for four hours. The phytochemical and surfactant mixture was centrifuged at 3500 rpm for 15 minutes at 10° C. and filtered before use, and then diluted in an equal volume of 2×MEM to give the undiluted preparation in 1×MEM.

1. Three plates were used to screen the three drug preparations. The concentrations needed to screen for antiviral activity were 1:2, 1:4, 1:8, and 1:16 in 1×MEM. There were four control compartments on each plate containing MEM without drug.

2. The growth media was removed from the compartments and 200 ul of HSV-1 was added to each compartment of the upper half of each plate. HSV-1 was diluted 1:5000 (2.0 ul of stock HSV-1 in 10 mL of MEM). The virus titer was $3\times10^6$ per mL.

3. The plates were incubated at 37° C. for four hours.

4. The inoculum was removed and one mL of the MEM containing drugs #1A–3A were added to the four compartments.

TABLE 4

| Concentration | Undiluted | 1:2 | 1:4 | 1:8 | 1:16 |
|---|---|---|---|---|---|
| Drug (ul) | 4000 | 2000 | 1000 | 500 | 250 |
| MEN (ul) | — | 2000 | 3000 | 3500 | 3750 |

5. Results: HSV-1, liquid overlay, composition added immediately after virus absorption.

TABLE 5

Drug #1A - HSV 1 Test Results

| Concentration | 1:2 | 1:4 | 1:8 | 1:16 | 1:32 |
|---|---|---|---|---|---|
| plaques | 70 | toxic | toxic | toxic | toxic | toxic |
| plaques | 68 | | | | | |
| plaques | 58 | | | | | |
| plaques | 74 | | | | | |
| Average | 70 | | | $IC_{50}$ | | |

Comments: These compartments have a fine precipitate over the cells. Benzalkonium chloride probably precipitates with the protein in the medium.

TABLE 6

Drug #2A - HSV 1 Test Results

| Concentration | 1:2 | 1:4 | 1:8 | 1:16 | 1:32 |
|---|---|---|---|---|---|
| plaques | 72 | — | — | — | 9* | 12* |
| plaques | 74 | — | — | — | 7 | 8 |
| plaques | 79 | — | — | — | 4 | 12 |
| plaques | 71 | — | — | — | 7 | 11 |
| Average | 70 | | | | | $IC_{50} > 1:32$ |

Comments: Although there were some plaques, they were very small.

TABLE 7

Drug #3A - HSV 1 Test Results

| Concentration | 1:2 | 1:4 | 1:8 | 1:16 | 1:32 |
|---|---|---|---|---|---|
| plaques | 72 | toxic | toxic | toxic | toxic | —* |
| plaques | 68 | | | | | — |
| plaques | 67 | | | | | — |

TABLE 7-continued

Drug #3A - HSV 1 Test Results

| Concentration | 1:2 | 1:4 | 1:8 | 1:16 | 1:32 |
|---|---|---|---|---|---|
| plaques | 70 | — | | | |
| Average | 70 | | | | $IC_{50} > 1:32$ |

Comments: Although there was some toxicity, this drug was very successful in inhibiting the virus, there did not appear to be any plaques.

EXAMPLES 23–27

Four 24-compartment plates were inoculated with fibroblasts.

Test Drug #1B=Benzalkonium chloride surfactant in an aqueous diluent. The benzalkonium chloride was prepared by making a 1:1000 dilution in water (10 ul in 10.0 mL of sterile water). This was filtered before use and diluted in an equal volume of 2xMEM to give 1:2000 dilution in 1xMEM. (500 ul drug plus 500 ul of 2xMEM).

Test Drug #2B=*Echinacea purpurea* powder (phytochemicals) in an aqueous solution. This preparation was a 50 mg/mL solution (250 mg in 5.0 mL of water) of *Echinacea purpurea* powder in sterile water. The mixture was vortexed and refrigerated for four hours. This *Echinacea* powdered preparation was centrifuged at 3500 rpm for 15 minutes at 10° C. and filtered before use, and diluted in an equal volume of 2xMEM to give the undiluted preparation in 1xMEM. (500 ul drug plus 500 ul of 2xMEM).

Test Drug #3B =*Echinacea purpurea* powder (phytochemicals) dissolved in benzalkonium chloride surfactant. This preparation was a 50 mg/mL solution (250 mg in 5.0 mL of benzalkonium chloride, 1:1000). The mixture was vortexed and refrigerated for four hours. The *Echinacea* phytochemicals and surfactants were centrifuged at 3500 rpm for 15 minutes at 10° C. and filtered before use, and then diluted in an equal volume of 2xMEM to give the preparation in 1xMEM (500 ul drug plus 500 ul of 2xMEM).

Test Drug #4B=*Echinacea purpurea* powder (phytochemicals) in an aqueous solution (diluent) and then mixed with benzalkonium chloride surfactant at a ratio of 1:1000. This preparation was a 50 mg/mL solution (250 mg in 5.0 mL in 5.0 mL of water) of *Echinacea purpurea* powder in sterile water. The mixture was vortexed and refrigerated for four hours. The aqueous phytochemicals were centrifuged at 3500 rpm for 15 minutes at 10° C. and filtered before use. This preparation was diluted in an equal volume of benzalkonium chloride at a ratio of 1:1000, to get the *Echinacea*-benzalkonium chloride mixture. This mixture was diluted with equal volume of 2xMEM to give the 1:4 preparation in 1xMEM (500 ul drug #1 and 250 ul drug #2 plus 500 ul of 2xMEM).

1. Four plates were used to screen the four drug preparations. The concentrations needed to screen for antiviral activity were 1:20, 1:40, 1:80, and 1:160 and 1:320 in 1xMEM. There were four control compartments on each plate containing MEM without drug.

2. The growth media was removed from the compartments and 200 ul of HSV-1 was added to each compartment of the upper two rows of each plate. HSV-1 was diluted 1:5000(2.0 ul of stock HSV-1 in 10 mL of MEM). The virus titer was 3x10$^6$ per mL. Also, 200 ul of HSV-2 was added to each compartment of the lower half of each plate. HSV-2 was diluted 1:2,000 (5.0 ul of stock HSV-2 in 10 mL of MEM). The virus titer was 6x10$^5$ per mL.

3. The plates were incubated at 37° C. for four hours.
4. The inoculum was removed and one mL of the MEM containing drugs #1–4 was added to the four compartments.

TABLE 8

| Concentrate | 1:20 | 1:40 | 1:80 | 1:160 | 1:320 |
|---|---|---|---|---|---|
| Drug (ul) | 400 | 200 | 100 | 50 | 25 |
| MEM (ul) | 3600 | 3800 | 3900 | 3950 | 3975 |

5. Results: HSV-1, liquid overlay, drugs added immediately after virus absorption.

TABLE 9

Drug #1B - HSV 1 Test Results

| Concentration | 1:20 | 1:40 | 1:80 | 1:160 | 1:320 |
|---|---|---|---|---|---|
| plaques | 37 | toxic | toxic | toxic | toxic | 15?* |
| plaques | 45 | | | | | 18?* |
| Average | 41 | | | $IC_{50}$ | | |

Comments: Slightly toxic, test was difficult to read.

HSV-2, liquid overlay, drugs added immediately after virus absorption.

TABLE 10

Drug #1B - HSV 2 Test Results

| Concentration | 1:20 | 1:40 | 1:80 | 1:160 | 1:320 |
|---|---|---|---|---|---|
| plaques | 38 | toxic | toxic | toxic | toxic | 21 |
| plaques | 42 | | | | | 17 |
| Average | 40 | | | | | 19 $IC_{50} > 1:320$ |

Comments: Test was too toxic to give a good reading.

TABLE 11

Drug #2B - HSV 1 Test Results

| Concentration | 1:20 | 1:40 | 1:80 | 1:160 | 1:320 |
|---|---|---|---|---|---|
| plaques | 39 | 2* | 8* | 23* | 24 | 44 |
| plaques | 40 | 3 | 18 | 11 | 28 | 38 |
| Average | 40 | 3 | 13 | 17 | 26 | $IC_{50} > 1:80$ |

Comments: Small plaques.

TABLE 12

Drug #2B - HSV 2 Test Results

| Concentration | 1:20 | 1:40 | 1:80 | 1:160 | 1:320 |
|---|---|---|---|---|---|
| plaques | 48 | 21 | 33 | | | |
| plaques | 52 | 22 | 38 | | | |
| Average | 50 | 21.5 | 35.5 | | | $IC_{50} > 1:20$ |

TABLE 13

Drug #3B - HSV 1 Test Results

| Concentration | 1:20 | 1:40 | 1:80 | 1:160 | 1:320 |
|---|---|---|---|---|---|
| plaques | 44 | 1* | 17 | 31 | 37 | |
| plaques | 46 | — | 16 | 28 | 27 | |
| Average | 45 | — | 17 | 30 | 32 | $IC_{50} > 1:40$ |

Comments: Although there was some toxicity, drug very successful there did not appear to be any plaques.

TABLE 14

Drug #3B - HSV 2 Test Results

| Concentration | 1:20 | 1:40 | 1:80 | 1:160 | 1:320 | |
|---|---|---|---|---|---|---|
| few cells | | 11* | 27 | 30 | 35 | |
| plaques | 44 | 10 | 32 | | | |
| Average | 44 | 11 | 29.5 | | | IC$_{50}$ > 1:20 |

Comments: A difficult test to get a really good reading. However the drug has successful inhibitory activity.

TABLE 15

Drug #4B - HSV 1 Test Results

| Concentration | 1:40 | 1:80 | 1:160 | 1:320 | 1:640 | |
|---|---|---|---|---|---|---|
| plaques | 47 | toxic | toxic | toxic | 33 | |
| plaques | 48 | | | 28 | | |
| Average | 48 | | | 30 | | IC$_{50}$ > 1:320 |

Comments: Too toxic at the higher levels. Nonetheless, there was inhibitory activity at 1:320

TABLE 16

Drug #4B - HSV 2 Test Results

| Concentration | 1:40 | 1:80 | 1:160 | 1:320 | 1:640 | |
|---|---|---|---|---|---|---|
| plaques | 38 | toxic | toxic | toxic | 2* | 16 |
| plaques | 40 | | | | 4 | 20 |
| Average | 39 | | | | 3 | 18 IC$_{50}$ > 1:640 |

Comments: Toxicity probably due to the benzalkonium chloride. The drug at the 1:320 dilution showed very strong inhibitory activity.

The in vitro tests of Examples 23–27 used raw materials which were not refined. Nevertheless, the tests demonstrate surprisingly good viral inhibitory activity and a probable synergy between the constituents.

In the preceding in vitro tests where Drugs #3, 3A and 3B, were *Echinacea purpurea* phytochemicals extracted and combined with benzalkonium chloride surfactant, the resultant medicine, demonstrated the greater antiviral activity, and most remarkably demonstrated a synergy between the components: *Echinacea purpurea* and benzalkonium chloride. This can possibly be explained by a shared stability and enhanced reactivity between the two components. The benzalkonium chloride in the synergistic mixture exhibited a lesser degree of toxicity and the synergistic combination (medicine) exhibited a greater degree of antiviral activity, particularly with HSV-2.

Surfactants

While benzalkonium chloride is the preferred surfactant for best results, in some circumstances it may be desirable to use other quaternary ammonium surfactants or other surfactants.

The quaternary ammonium compound can be dicocodimonium chloride, which is also known as dicoco alkyldimethyl, chlorides or dicoco dimethyl ammonium chloride or Di-C8-18-alkyldimethyl, chlorides. This can be used in combination with isopropanol, such as 20–30% isopropanol. The preferred source of quaternary compound comprises: 70–80% quaternary ammonium compound and less than 0.03% methyl chloride, has a specific gravity of about 0.87 at 115 degrees F., a vapor pressure of 33 mm/Hg at 68 degrees F., an initial boiling point of 180 degrees F. at 760 mm/Hg, and a volatility of 20–30%, and is produced under the brand name CarSpray 300 by Witco Corporation, Dublin, Ohio, USA. The quaternary compound can provide disinfecting qualities and serves as a fungicide to treat fungus and yeast infections.

Other quaternary ammonium compounds may be useful, such as produced under the brand name Jet Quat 2C-75 by Jetco Chemicals, Inc. of Corsicana, Tex., USA, or produced under the brand names Carspray 400 and Carnauba Spray 200 by Witco Corporation, Dublin, Ohio, USA, or containing 9% denatured ethyl alcohol such as sold under the brand name BTC 2125M by Stephan Company, Northfield, Ill., USA, or the following MAQUAT products comprising n-alkyl dimethyl benzyl ammonium chloride produced by Mason Chemical Company, Arlington Heights, Ill., USA. LC-12S (67% C12, 25% C14, 7% C16, 1% C18), MC 1416 (5% C12, 60% C14, 30% C16, 5% C18), MC1412 (40% C12, 50% C14, 10% C16), SC-18 stearyl paste or flake (5% C16, 95% C18), TC-76 or MQ-2525 (5% C12, 60% C14, 30% C16, and 5% C18) and MC6025-50% (25% C12, 60% C14 and 15% C16). Jet Quat 2C-75 comprises: 50–75% dicoco dimethyl quaternary ammonium chloride, 20–50% isopropyl alcohol, has a specific gravity of 0.88 and a boiling point of 180 degrees F. CarSpray 400 comprises: 55–65% quaternary ammonium compounds, 20–30% amines, C14–18 & C16–18 unsaturated, alkyl, ethoxylated, 10–20% isopropanol, and less than 0.03% methyl chloride, and has a specific gravity of approximate 0.88 at 75 degrees, F., a vapor pressure of 33 mm/Hg at 68 degrees F., an initial boiling point of 180 degrees F. at 760 mm/Hg, and a volatility of 10–20%. Carnauba Spray 200 comprises: 50–60% quaternary ammonium compounds, 10–20% isopropanol, 15–25% water, 1–10% alkoylated carnauba wax, and less than 0.03% methyl chloride, and has a specific gravity of about 0.90 at 80 degrees F., a vapor pressure of 33 mm/Hg at 68 degrees F., an initial boiling point of 180 degrees F. at 760 mm/Hg, and a volatility of 20–40%.

Nonionic surfactants are surface-active compounds which do not ionize in water solution. Often times these possess hydrophilic characteristics by virtue of the presence therein of an oxygenated chain (e.g., a poly-oxyethylene chain), the lyophilic portion of the molecule being derived from fatty acids, phenols, alcohols, amides or amines. Exemplary compounds are the poly-(ethylene oxide) condensates of alkyl phenols, e.g. the condensation product formed from one mole of nonyl phenol and ten moles of ethylene oxide, and the condensation products of aliphatic alcohols and ethylene oxide, e.g. the condensation product formed from 1 mole of tridecanol and 12 moles of ethylene oxide.

The nonionic surfactants can comprise phenol ethoxylates comprising a condensate product of ethylene oxide and an alkyl phenol or an aliphatic alcohol. The nonionic surfactants preferably comprise nonophenol ethoxylate such as T-DET, and/or octaphenol ethoxylate. The nonionic surfactants are reaction products of ethylene oxide and nonolphenol and/or octalphenol. The ratio of the phenol to the ethylene oxide can range from 2:20 to 4:16 and preferably is about 8:12.

Nonionic synthetic surfactants can comprise nonionic detergents. Nonionic synthetic surfactants can also be formed by condensing ethylene oxide with a hydrophobic base formed by the condensation of propylene oxide with propylene glycol. The hydrophobic portion of the molecule which, of course, exhibits water insolubility has a molecular weight of from about 1200 to 2500. The addition of polyoxyethylene radicals to this hydrophobic portion tends to increase the water solubility of the molecule as a whole and the liquid character of the product can be retained up to the point where polyoxyethylene content is about 50% of the total weight of the condensation product. Other nonionic synthetic surfactants can include: the polyethylene oxide condensates of alkylphenols, e.g. the condensation products of alkylphenols or dialkylphenols wherein the alkyl group contains from about 6 to 12 carbon atoms in either a straight chain or branched chain configuration, with ethylene oxide. The ethylene oxide can be present in amounts equal to 8 to 25 moles of ethylene oxide per mole of alkylphenol. The alkyl substituent in such compounds can be derived from polymerized propylene, diisobutylene, n-octene, or n-nonene.

Nonionic surfactants can also be produced from the condensation of ethylene oxide with the reaction product of propylene oxide and ethylenediamine, e.g. compounds containing from about 40% to about 80% polyoxyethylene by weight and having a molecular weight of from about 5,000 to about 11,000 resulting from the reaction of ethylene oxide groups with a hydrophobic base comprising the reaction product of ethylenediamine and excess propylene oxide; the base having a molecular weight on the order of 2,500 to 3,000.

Other nonionic surfactants include the condensation product of aliphatic alcohols having from 8 to 18 carbon atoms, in either straight chain or branched chain configuration, with ethylene oxide, e.g. a coconut alcohol ethylene oxide condensation having from 10 to 30 moles of ethylene oxide per mole of coconut alcohol, and the coconut alcohol fraction having from 10 to 14 carbon atoms.

Further nonionic surfactants include long chain tertiary amine oxides corresponding to the following general formula:

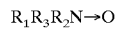

wherein R1 is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use include: dimethyldodecylamine oxide, dimethyloctylamine oxide, dimethyldecylamine oxide, dimethyltetradecylamine oxide, and dimethylhexadecylamine oxide.

Other nonionic surfactants can include: long chain tertiary phosphine oxides corresponding to the following general formula

wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are: dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, dipropyldodecylphosphine oxide, bis-(2-hydroxymethyl) dodecylphosphine oxide, bis-(2-hydroxyethyl)dodecylphosphine oxide, (2-hydroxy propyl)methyltetradecylphosphine oxide, dimethyloleylphosphine oxide, and dimethyl-(2-hydroxydodecyl) phosphine oxide.

In some circumstances it may be useful to use other surfactants such as: another cationic surfactant, an ampholytic surfactant or a zwitterionic surfactant.

The cationic surfactants can include cationic detergents. The cationic surfactants comprise compounds which ionize in an aqueous medium to give cations containing the lyophilic group. Typical of these compounds are the quaternary ammonium salts which contain an alkyl group of about 12 to about 18 carbon atoms, such as lauryl benzyl dimethyl ammonium chloride.

Ampholytic surfactants are compounds having both anionic and cationic groups in the same molecule. Exemplary of such compounds are derivatives of aliphatic amines which contain a long chain of about 8 to about 18 carbon atoms and an anionic water solubilizing group, e.g., carboxysulfo, sulfo or sulfato. Examples of ampholytic detergents are: sodium-3-dodecylaminopropane sulfonate, sodium-N-methyl taurate, and related substances such as higher alkyl disubstituted amino acids, betaines, thetines, sulfated long chain olefinic amines, and sulfated imidazoline derivatives.

Zwitterionic surfactants can include synthetic detergents. Zwitterionic surfactants are generally derivatives of aliphatic quaternary ammonium compounds in which the aliphatic radical can be a straight chain or branched and wherein one of the aliphatic substituents contains from about 8 to 18 carbon atoms and one contains an anionic water solubilizing group, e.g., carboxy, sulfo, or sulfato. Examples of compounds falling within this definition are: 3-(N,N-dimethyl-N-hexadecyl ammonio)-propane-1-sulfonate and 3-(N,N-dimethyl-N-hexadecyl ammonio) -2-hydroxy propane-1-sulfonate.

Treatment

The preferred medical treatment comprises a method for use in treating herpes virus or other infectious diseases by resolving the physical symptoms of an infectious outbreak of herpes simplex virus 1 or 2 (HSV 1 or HSV 2) or other infectious microbial diseases within 1–30 hours. This is accomplished by topically applying the above described preferred antimicrobial compound (medicine) on the infected area of the herpes simplex virus or other infectious microbial disease, and maintaining the antimicrobial compound on the infected area for 1–30 hours, preferably at least 10 hours. The antimicrobial compound (medicine) can be applied in the manner previously described and most preferably coats the infected area. Desirably, the infected area is rinsed (washed) and dried to remove any soap or residue on the infected area before the antimicrobial compound (medicine) is applied. Preferably, vesicular eruption of herpes virus are resolved in 19–24 hours and herpes lesions are healed by maintaining the above described most preferred medicine on the infection for 19–24 hours.

Among the many advantages of the medical treatment and medicine (compositions) of the invention are:

1. Superior results in ending the pain of herpes simplex viral infections and other microbial infections.
2. Outstanding performance in rapidly resolving outbreaks of herpes simplex virus and other microbial diseases.
3. Potentially saves lives of neonates and animals.
4. Reduces risk of blindness in newborns.
5. Reduces worldwide economic loss from herpes and other microbial diseases.
6. Resolves the serious emotional and mental anguish of herpes sufferers.
7. Readily available materials (ingredients).
8. Economical.

9. Safe.
10. Easy to use.
11. Dependable.
12. Effective.

Although embodiments of the invention and examples have been shown and described, it is to be understood that various modifications and substitutions, as well as rearrangements of parts, components, and process steps, methods and treatment, can be made by those skilled in the art without departing from the novel spirit and scope of this invention.

What is claimed is:

1. A method for use in treating viral diseases, comprising the steps of:
   substantially inhibiting infections from viral diseases by applying a composition of about 2% to about 90% by weight *Echinacea purpurea* providing viral microbe inhibitors and from substantially greater than 0.01% to about 0.8% by weight of a surfactant on an infected region;
   maintaining said composition comprising said *Echinacea purpurea* providing said microbe inhibitors and said surfactant on said infected region until external symptoms and physical manifestations of the infection substantially disappear about the infected region;
   said viral diseases comprising a viral disease selected from the group consisting of herpes simplex virus 1, herpes simplex virus 2, papilloma virus, varicella zoster virus (herpes zoster), and cytomegalovirus;
   said microbe inhibitors are applied to said infected region to substantially inhibit said infections; and
   said surfactant is a quaternary ammonium salt surfactant selected from the group consisting of alkyl dimethylbenzylammonium chloride, benzalkonium bromide, benzalkonium chloride, alkylbenzyldimethylammonium chloride, alkyldimethybethylbenzylammonium chloride, n-alkyldimethylbenzylammonium chloride, diisobutylphenoxyethoxethyl dimethylammonium chloride, n-dimethylbenzylammonium chloride, octyldecyldimethylammonium chloride, didecyldimethylammonium chloride, dioctyldimethylammonium chloride, diakyldimethylammonium chloride, octyldecylidimethylammonium chloride, laurryl dimethylbenzylammonium chloride, o-benzyl-p-chlorophenol, diethyldimethylammonium chloride, doctyldimethylammonium chloride, alkyldimethylbenzylammonium chloride, and alkylbenzyldimethylammonium chloride.

2. A method in accordance with claim 1, wherein:
   said composition of about 2% to about 20% by weight *Echinacea purpurea* providing said microbe inhibitors and from substantially more than 0.01% to about 0.8% by weight of said surfactant are applied on an external portion of an animal selected from the group consisting of a dog, cat, bird, horse, cow, sheep, swine, farm animal and rodent; and
   said composition of about 2% to about 20% by weight *Echinacea purpurea* providing said microbe inhibitors and from substantially more than 0.01% to about 0.8% by weight of said surfactant are applied by directly contacting said infected region of said animal with said composition of about 2% to about 20% by weight *Echinacea purpurea* providing said microbe inhibitors and from substantially more than 0.01% to about 0.8% by weight of said surfactant.

3. A method in accordance with claim 1, wherein:
   said composition of about 2% to about 90% by weight *Echinacea purpurea* providing said microbe inhibitors and from substantially more than 0.01% to about 0.8% to by weight of said surfactant and said quarternary ammonium salt surfactant are applied and maintained on an infected region of a homo sapien until the external appearance of an eruption and outbreak of said infection substantially subside; and
   said composition of about 2% to about 90% by weight *Echinacea purpurea* providing said microbe inhibitors comprise a phytochemical selected from the group consisting of: echinacen; echinacen B; echinaceine; echinacoside; caffeic acid ester; echinolone; enzymes; glucuronic acid; inulini; inuloid; pentadecadiene; polyacelytene compounds; polysaccharides; arabinogalactan; rhamnose; tannins; PSI (a 4-O-methylglucoronoarabinoxylan, $M_r$ 35Kd); PSII (an acid rhamnoarbinogalactain, $M_r$ 450 kD); cynarin; 1,5-di-ocaffeoylquinic acid; chicoric acid; 2,3-O-di-caffeoyltartaric acid; borneol; borneol acetate; pentadeca-8(z)-en-zone; germacrene D; caryophyllene; caryophyllene epoxide; anthocyanin, pyrrolizidine alkaloid, lipophilic amide; isobutylamide; polyacetylene; anthocyanin; 3-O-B-D-glucopyranoside; 3-O-(6-O-malonyl-B-D-glucopyranoside); tussilagine; isotussilagine; isomeric dodeca isobutylamide; tetraenoic acid; carophylenes.

4. A method in accordance with claim 1, wherein:
   said composition of about 2% to about 90% by weight *Echinacea purpurea* providing said microbe inhibitors and from substantially more than 0.01% to about 0.8% by weight of said surfactant are applied substantially simultaneously on the infected region with said surfactant and a carrier; and
   said carrier comprises a member selected from the group consisting of an aqueous carrier, water, glycerin, mineral oil, silica, talc, natural resins, synthetic resins, pyrethrum, talc, thiocyannates, phthalates, cottonseed oil, coconut oil, pine oil, vegetable oil, seed oil, nut oil, fish oil, animal oil, alcohol, corn meal, beeswax, carnauba wax, beta carotene, garlic oil, camphor oil, soluble vitamins, soluble minerals, rape seed oil, olive oil, lipsomes, ascorbic acid, primrose oil, pheynogeol, grape seed oil, lanolin, collagen, herbs, aloe vera, bee pollen, royal jelly, chondroitin sulfate, sea vegetables, fatty acids, lechithin, bioflavinoids, grain oil, grain powder, algae, teas, vinegars, acidophilus, cell salts, glandulars, amino acids, psyllium, plant derivatives, fruit derivates, and a sterile carrier.

5. A method for use in treating viral diseases, comprising the steps of:
   substantially resolving the physical symptoms of an infectious outbreak of viral diseases within about 1.0 hours to about 30 hours by topically applying an antimicrobial compound of about 40% to about 60% by weight *Echinacea purpurea* and from substantially more than 0.01% to about 0.8% by weight quartenary ammonium salt surfactant to an area infected with viral disease;
   said viral disease selected from the group consisting of herpes simplex virus 1, herpes simplex virus 2, papilloma virus, varicella zoster virus (herpes zoster), and cytomegalovirus;
   maintaining said antimicrobial compound of about 40% to about 60% by weight *Echinacea purpurea* and from substantially more than 0.01% to about 0.8% by weight quaternary ammoniun salt surfactant on said infected area for about 10 hours to about 30 hours;

compound comprises by weight:

said 40% to about 60% by weight *Echinacca purpurea* comprising a a phytochemical selected from the group consisting antimicrobial isolates selected from the group consisting of: echinacen; echinacen B; echinaceine; echinacoside; caffeic acid pester; echinolone; enzymes; glucuronic acid; inulin; inuloid; pentadecadiene; polyacetylene compounds; polysaccharides; arabinogalactan; rhamnose; tannins; PSI (a 4-0-methylglucoronoarabinoxylan, Mr 35Kd); PSII (an acid rhamnoarbinogalactain, Mr 450 kD); cynarin; 1,5-di-0-caffeoylquinic acid; chicoric acid; 2,3-0 di-caffeoyltartaric acid; borneol; borneol acetate; pentadeca-8(z)-en-zone; germacrene D; caryophyllene; caryophyllene epoxide; anthocyanin, pyrolizidine alkaloid, lipophilic amide; isobutylamide; polyacetylene; anthocyanin; 3-0-B-D-glucopyranoside; 3-0-(6-0-malonyl-B-D-glucopyranoside); tussilagine; isotussilagine; isomeric dodeca isobutylamide; tetraenoic acid; carophylenes; and combinations thereof;

said 0.01% to about 0.8% quaternary ammonium salt surfactant comprising a member selected from the group consisting of alkyl dimethylbenzylammonium chloride, benzalkonium halide, benzalkonium bromide, benzathonium chloride, alkylbenzyldimethylammonium chloride, alkyldimethybethylbenzylammonium chloride, n-alkyldimethylbenzylammonium chloride, diisobutylphenoxyethoxethyl dimethylammonium chloride, n-dimethylbenzylammonium chloride, octyldecyldimethylammonium chloride, didecyldimethylammonium chloride, dioctyldimethylammonium chloride, diakyldimethylammonium chloride, octyldecylidimethylammonium chloride, laurryl dimethylbenzylammonium chloride, o-benzyl-p-chlorophenol, dideryldimethylammonium chloride, doctyldimethylammonium chloride, alkyldimethylbenzylammonium chloride, and alkylbenzyldimethylammonium chloride; and an aqueous diluent and carrier for said microbial compound of about 40% to about 60% by weight *Echinacea purpurea* and from substantially more than 0.01% to about 0.8% by weight quaternary ammonium salt surfactant, and the overall ratio of said aqueous diluent to said antimicrobial compound of about 40% to about 60% by weigtht *Echinacea purpurea* and from substantially more than 0.01% to about 0.8% by weight quaternary ammonium salt surfactant ranges from about 2:1 to about 100:1.

6. A method in accordance with claim 5, wherein:

said area infected with said viral disease is rinsed and dried to remove any soap or residue on the area infected with said viral disease before said antimicrobial compound of about 40% to about 60% by weight *Echinacea purpurea* and from substantially more than 0.01% to about 0.8% by weight quaternary ammonium salt surfactant is applied; and said ammonium salt surfactant comprises benzalkonium chloride and the surfactant ratio of said aqueous carrier to said benzalkonium chloride ranges from about 30,000:1 to about 250:1.

7. A method in accordance with claim 5, wherein:

said antimicrobial compound of about 40% to about 60% by weight *Echinacea purpurea* and from substantially more than 0.01% to about 0.8% by weight quatenary ammonium salt surfactant are applied topically to the area infected by a viral disease by a procedure selected from the group consisting of spraying, dabbing, dusting, swobbing, sponging brushing, pouring, dispensing, covering and coating; and said area infected with said viral disease is selected from the group consisting of oral mucosa, nasal mucosa, vaginal tissue, labial tissue, anal tissue, periacinal tissue, lips, cutaneous tissue, ocular tissue, conjunctive, and eye lids.

8. A method in accordance with claim 5, wherein:

vesicular eruption of said herpes simplex virus are resolved in about 19 hours to about 24 hours by maintaining said antimicrobial compound of about 40% to about 60% by weight *Echinacea purpurea* and from substantially more than 0.01% to about 0.8% by weight quatenary ammonium salt surfactant on said are infected with said viral disease for about 19 hours to about 24 hours/.

9. A method for topical treatment of active phase lesions resulting from herpes, comprising the steps of:

conditioning and treating an active phase herpes lesion on skin or mucosa resulting from herpes by sequentially moistening and powdering said active phase herpes lesion;

said moistening comprising wetting the active phase lesion on skin or mucosa with an aqueous solution of benzalkonium halide and water;

said herpes selected from the group consisting of HSV1, herpes labialis, keratitis, HSV2, and genital herpes;

said benzalkonium halide selected form the group consisting of benzalkonium chloride and benzalkonium fluoride;

said powdering the active phase herpes lesion comprising dusting and coating the wetted active phase herpes lesion with powdered *Echinacea purpurea* to form a coating of powdered *Echinacea purpurea,* benzalkonium halide, water on the wetted active phase lesion; and treating the active phase lesion by maintaining the coating of powdered *Echinacea purpurea,* benzalkonium chloride and water on the wetted active phase herpes lesion until the active phase herpes lesion of HSV1, herpes, labalis, keratitis. HSV2, or genital herpes is substantially resolved.

10. A method for topical treatment of active phase lesions resulting from herpes, comprising the steps of:

coating and treating an active phase lesion resulting from herpes;

said herpes selected from the group consisting of HSV1, herpes labialis, keratitis, HSV2, and genital herpes;

said coating comprising substantially covering said active phase lesion with *Echinacea purpurea* and benzalkonium halide;

said benzalkonium halide selected form the group consisting of benzalkonium chloride and benzalkonium fluoride; and treating the active phase lesion by maintaining the coating of *Echinacea purpurea* and benzalkonium halide on the active phase lesion until the active phase lesion is substantially resolved.

* * * * *

UNITED STATES PATENT AND TRADEMARK OFFICE
CERTIFICATE OF CORRECTION

PATENT NO. : 6,946,490 B2 Page 1 of 1
DATED : September 20, 2005
INVENTOR(S) : Meryl Squires It is certified that error appears in the above-identified patent and that said Letters Patent is hereby corrected as shown below:

Column 22,
Line 26, correct "; carophylenes." to -- ; and carophylenes. --.

Column 24,
Line 39, correct ", water on the wetted active phase lesion;" to -- , and water on the wetted active phase lesion; --.

Signed and Sealed this

Twenty-fourth Day of January, 2006

JON W. DUDAS
*Director of the United States Patent and Trademark Office*